(12) United States Patent
Biondolillo

(10) Patent No.: US 9,474,655 B1
(45) Date of Patent: Oct. 25, 2016

(54) UNDERGARMENTS WITH SANITARY ABSORBENT DEVICE HOLDER

(76) Inventor: Kathy Biondolillo, Parkland, FL (US)

( * ) Notice: Subject to any disclaimer, the term of this patent is extended or adjusted under 35 U.S.C. 154(b) by 0 days.

(21) Appl. No.: 13/353,399

(22) Filed: Jan. 19, 2012

Related U.S. Application Data

(63) Continuation-in-part of application No. 12/123,579, filed on May 20, 2008, now Pat. No. 8,100,876.

(51) Int. Cl.
*A61F 13/15* (2006.01)
*A61F 13/505* (2006.01)

(52) U.S. Cl.
CPC .............. *A61F 13/15* (2013.01); *A61F 13/505* (2013.01); *A61F 2013/5055* (2013.01)

(58) Field of Classification Search
CPC ........... A61F 13/505; A61F 13/15268; A61F 2013/15276; A61F 2013/5661
USPC .............. 604/385.14, 386, 387, 393, 385.19, 604/396, 385.11, 395, 385.15
See application file for complete search history.

(56) References Cited

U.S. PATENT DOCUMENTS

| 4,950,264 A | * | 8/1990 | Osborn, III | ....... A61F 13/15203 604/385.08 |
| 5,897,545 A | * | 4/1999 | Kline et al. | .................... 604/386 |
| 2003/0199844 A1 | * | 10/2003 | LaVon et al. | ............ 604/385.14 |

* cited by examiner

Primary Examiner — Jacqueline Stephens
(74) Attorney, Agent, or Firm — Glenn E. Gold, P.A.

(57) ABSTRACT

Undergarments with sanitary absorbent device holders include an undergarment body and a sanitary absorbent device holder carried by the undergarment body. The sanitary absorbent device holder is adapted to hold a sanitary absorbent device such as a tampon or sanitary napkin in a discreet or concealed manner as the undergarment is worn by a user. A sanitary absorbent device holder undergarment accessory can include a sanitary absorbent device holder carrier having a sanitary device holder attached thereto. The sanitary absorbent device holder undergarment accessory can be separatably attached to woman's underwear by any of a variety of configurations, including folding over a waistband and attaching a pair of holder panel leg band edges of the carrier together, attaching each holder panel leg band edge to a like edge of the underwear via an attachment interface, or any other reasonably known attachment configuration.

9 Claims, 16 Drawing Sheets

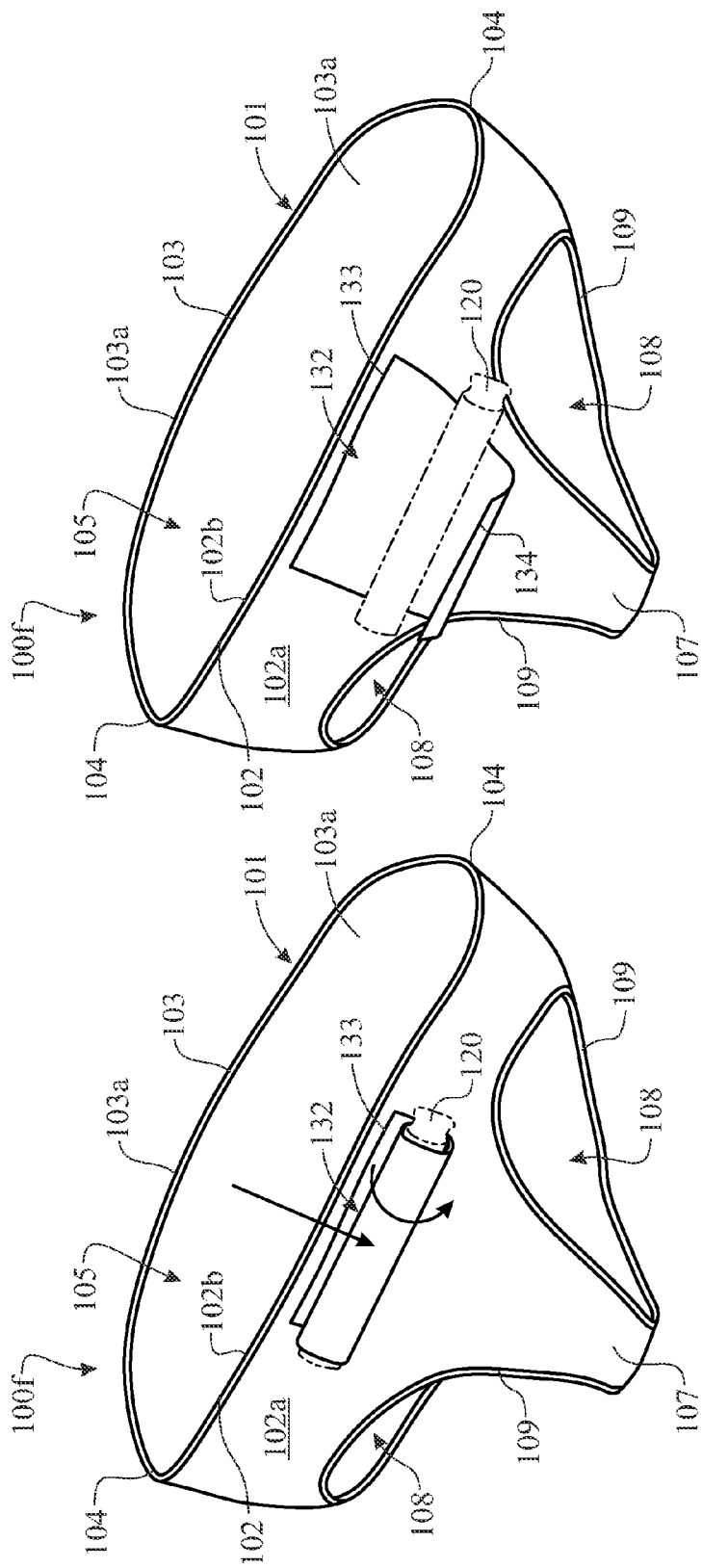

UNDERGARMENTS WITH SANITARY ABSORBENT DEVICE HOLDER

CROSS-REFERENCE TO RELATED APPLICATION

This Continuation-In-Part Utility Patent Application claims the benefit of co-pending U.S. Non-Provisional patent application Ser. No. 12/123,579, filed on May 20, 2008, which is incorporated herein in its entirety.

BACKGROUND OF THE INVENTION

1. Field of the Invention

The present invention relates to undergarments. More particularly, the present invention relates to an undergarment having a pocket that is adapted to hold a sanitary absorbent device such as a tampon or sanitary napkin in a discreet or concealed manner.

2. Discussion of the Related Art

Women frequently carry sanitary absorbent devices such as tampons and/or sanitary napkins so that the devices will be available when needed. These devices are typically stored and carried in a discreet or concealed manner such as in a purse or handbag, which the woman carries, for example. However, a purse may be undesirable to store and carry the devices since the tampons and/or sanitary napkins may occupy excessive space and/or contribute to disorganization of the contents of the purse. Furthermore, carrying a purse can be less than ideal at certain events, functions, schools, nightclubs, and work environments. Examples of potential occupations or events include: nursing/medical profession, clerks, cashiers, flight attendants, bar tenders, dancers, bikers, aerobics, stadium events, concerts, servers, young adolescents in school, executive meetings, etc., and the like.

Several teachings are known, placing a pocket on an inside of an undergarment. Placing items into a pocket on the inside of an undergarment can be uncomfortable. A woman's undergarment is normally designed for a tight fit. An object placed in a pocket located inside the undergarment is pressed against the wearer's body by the tight fitting garment causing discomfort. Furthermore, the internal pocket location hampers access to items placed inside the pocket, as the user is required to stretch the waistband outward.

Another teaching places pockets centered about each side of an undergarment. It is normally undesirable to place objects on the sides of one's body for many reasons. One example is a person's side is very susceptible to accidentally hitting an object. Another is the small radius of the curve about one's hip is not conducive to accessing an object within a side pocket. The tight curve tends to keep the pocket closed. Long objects that are not conducive to the natural bends of the human body, such as guns and knives, are placed along one's side for ease of access for use and ability to compensate for the natural bends.

Therefore, undergarments are needed which are fitted with holders suitable for holding a sanitary device such as a tampon or sanitary napkin in a discreet or concealed and comfortable manner.

SUMMARY OF THE INVENTION

The present invention is generally directed to undergarments, which are fitted with holders suitable for holding a sanitary device such as a tampon or sanitary napkin in a discreet or concealed manner. Each undergarment may be comfortably and discreetly worn by a user and hold a sanitary absorbent device such as a tampon or sanitary napkin in a secure and accessible manner.

In one aspect of the invention, the undergarment comprises:
an undergarment body, and
a sanitary absorbent device holder carried by the undergarment body.

In another aspect, the sanitary absorbent device holder may include a tampon pocket sized and configured to receive at least one tampon.

In yet another aspect, the sanitary absorbent device holder may include a sanitary napkin pocket sized and configured to receive at least one sanitary napkin. This pocket could also be used to hold other material or items.

In yet another aspect, the sanitary absorbent device holder may include a pair of spaced-apart elastic bands sized and configured to receive a tampon.

In yet another aspect, the sanitary absorbent device holder may include a scroll pocket sized and configured to receive a tampon.

In yet another aspect, a cover panel may be carried by the undergarment body and conceal the sanitary absorbent device holder.

In yet another aspect, the sanitary absorbent device holder may be carried by the cover panel.

In yet another aspect, a closure mechanism may be carried by the undergarment body and the sanitary absorbent device holder.

In yet another aspect, the sanitary absorbent device holder may be attached to a sanitary absorbent device holder undergarment accessory, wherein the sanitary absorbent device holder undergarment accessory is designed to be removably attached to a front or rear panel of a woman's panty or underwear.

In yet another aspect, the sanitary absorbent device holder undergarment accessory comprises:
  a sanitary absorbent device holder carrier having a first side and a second side;
  the sanitary absorbent device holder carrier segmented into a holder panel section and a rear panel section by a waistband fold, each panel section being bound by:
    the waistband fold,
    a pair of side edges, each side edge extending from a respective end of the waistband fold,
    a pair of leg band edges, each leg band edge extending from a distal end of each holder panel side edge, and
    a holder panel crotch edge extending between central ends of each of the leg band edges;
  an attachment interface provided between the holder panel section leg band edge and a mating rear panel section leg band edge; and
  a sanitary device holder attached to a first side of the holder panel section,
  wherein the sanitary absorbent device holder carrier is designed to be folded along the waistband fold, placed straddling the waistband fold over a waistband of a woman's underwear and secured in located by engaging the attachment interface between the holder panel section leg band edge and the mating rear panel section leg band edge at a position proximate a leg opening of the woman's underwear.

In yet another aspect, the sanitary absorbent device holder undergarment accessory further comprises a holder access port provided through the device holder support body.

In yet another aspect, the sanitary absorbent device holder undergarment accessory straddles the waistband of the underwear.

In yet another aspect, the sanitary absorbent device holder undergarment accessory straddles the waistband of the underwear and is secured about a leg band edge.

In yet another aspect, the sanitary absorbent device holder undergarment accessory comprises an attachment interface located on the holder body at a position proximate each leg band edge.

In yet another aspect, the attachment interface is located on each side of the holder body at a position proximate each leg band edge.

In yet another aspect, the sanitary absorbent device holder undergarment accessory is reversible, enabling attachment in either an exposed holder orientation or a conceal holder orientation.

In yet another aspect, the sanitary absorbent device holder undergarment accessory comprises:
- a sanitary absorbent device holder carrier formed to contour to a front panel of a woman's underwear having a waistband edge, a pair of leg band edges extending angularly downward from a respective end of the waistband edge, and a crotch edge extending between opposite ends of the leg band edges;
- a sanitary device holder attached to the sanitary absorbent device holder carrier;
- a first attachment interface assembled to the sanitary absorbent device holder carrier at a position located proximate each leg band edge; and
- a mating attachment interface assembled to a woman's underwear at a position located proximate each leg band edge, wherein the first attachment interface and the mating attachment interface are separatably engaging,
- wherein the sanitary absorbent device holder carrier provides access to the sanitary device holder when the sanitary absorbent device holder carrier is attached to the woman's underwear.

In yet another aspect, the sanitary device holder is provided upon a concealed surface of the sanitary absorbent device holder carrier.

In yet another aspect, the sanitary device holder is provided upon an exposed surface of the sanitary absorbent device holder carrier.

In yet another aspect, the sanitary device holder is vertically oriented.

In yet another aspect, the sanitary device holder is horizontally oriented.

In yet another aspect, the sanitary device holder designed to be moisture resistant.

In yet another aspect, the sanitary absorbent device holder undergarment accessory comprises:
- a woman's underwear comprising a front panel and a rear panel the front panel and rear panel defining a waistband, a pair of leg openings, and a crotch section formed between each of the pair of leg openings;
- a sanitary device holder attached to an exposed surface of the woman's underwear; and
- a sanitary absorbent device holder cover panel defined by a waistband edge section and a holder panel unsecured edge section, wherein the sanitary absorbent device holder cover panel waistband edge is attached to the woman's underwear proximate a underwear waistband edge;
- wherein the sanitary absorbent device holder cover panel covers the sanitary device holder and provides access to the sanitary device holder by raising the free edge of the cover panel.

These and other aspects, features, and advantages of the present invention will become more readily apparent from the attached drawings and the detailed description of the preferred embodiments, which follow.

BRIEF DESCRIPTION OF THE DRAWINGS

The preferred embodiments of the invention will hereinafter be described in conjunction with the appended drawings provided to illustrate and not to limit the invention, in which:

FIG. 8 presents front perspective view of another exemplary embodiment of a sanitary absorbent device holder containing undergarment, utilizing a scrolling tampon retainer provided on the undergarment and a tampon (shown in phantom) secured in the rolled-up scrolling tampon retainer;

FIG. 9 presents front perspective view of the sanitary absorbent device holder containing undergarment introduced in FIG. 8, illustrating the scrolling tampon retainer in an unrolled, extended configuration;

Like reference numerals refer to like parts throughout the several views of the drawings.

DETAILED DESCRIPTION OF REPRESENTATIVE EMBODIMENTS

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. In other implementations, well-known features and methods have not been described in detail so as not to obscure the invention. For purposes of description herein, the terms "upper", "lower", "left", "right", "front", "back", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments that may be disclosed herein are not to be considered as limiting, unless the claims expressly state otherwise.

Shown throughout the FIGS., the present invention is generally directed to undergarments, more specifically women's panties that are fitted with holders suitable for storing and retaining a sanitary device such as a tampon or sanitary napkin in a discreet or concealed manner. Each embodiment of the undergarment may be comfortably and discreetly worn by a user and hold a sanitary absorbent device, such as a tampon or sanitary napkin, in a secure and accessible manner.

Figure 1:
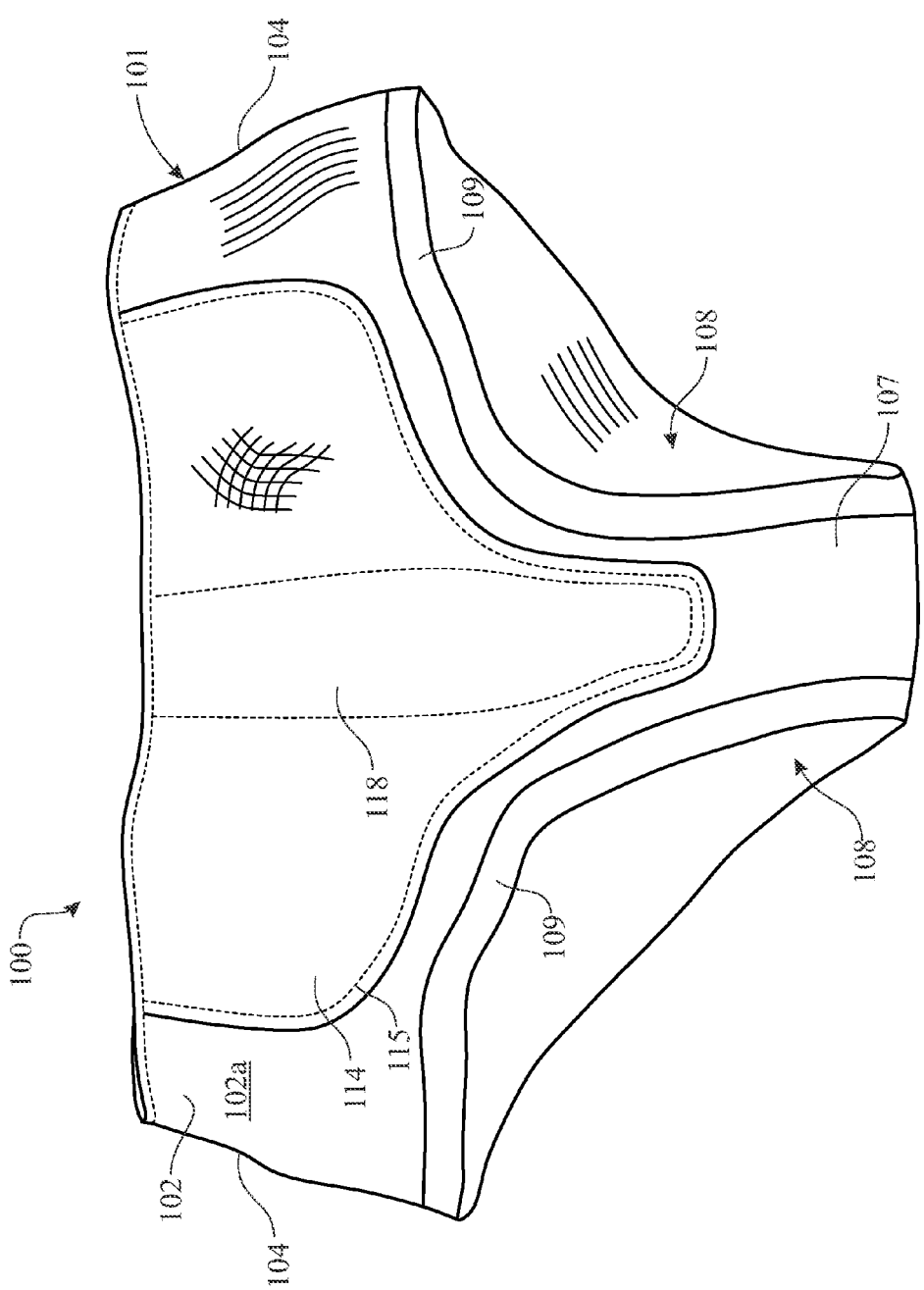
FIG. 1 presents a front view of a first exemplary embodiment of an undergarment comprising a sanitary absorbent device holder, with a vertically-oriented tampon pocket provided on the undergarment.
Figure 2:
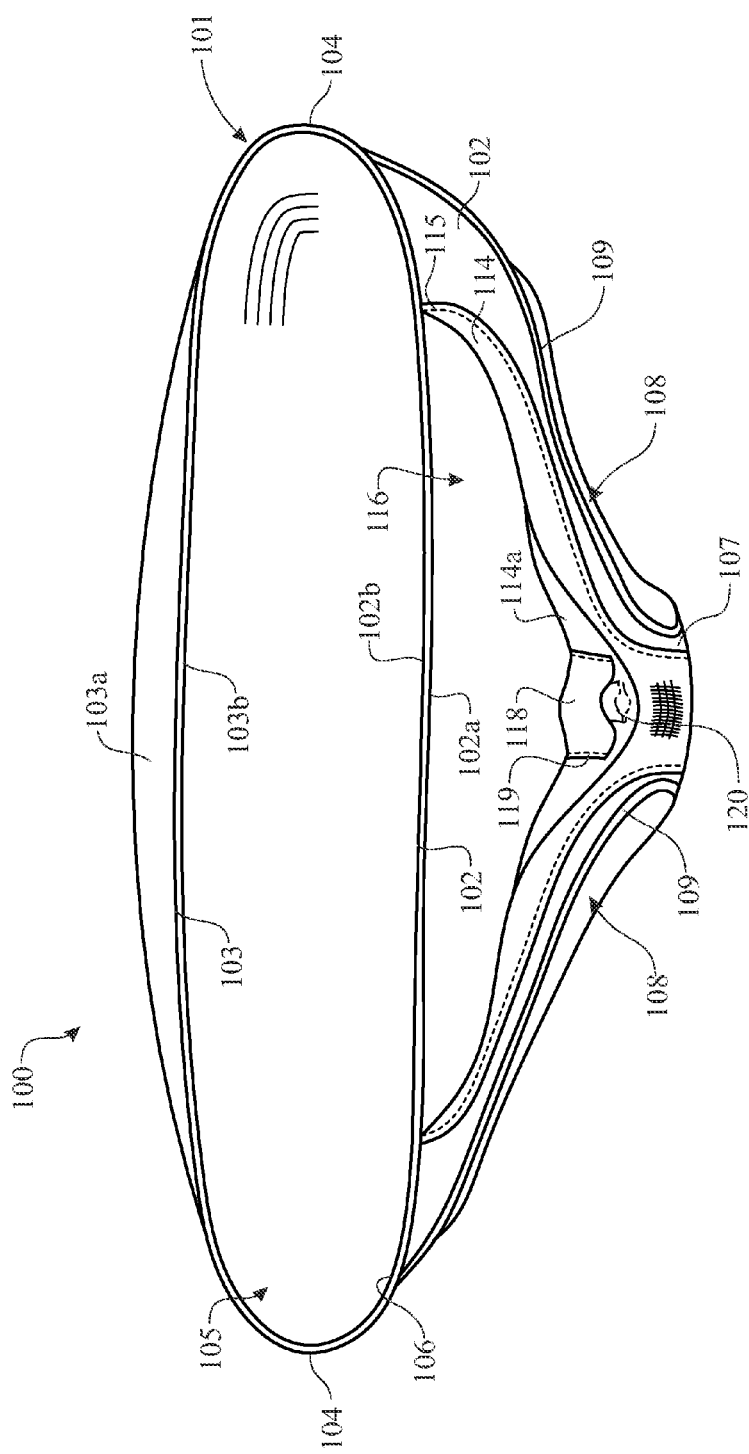
FIG. 2 presents a top perspective view of the exemplary embodiment of the sanitary absorbent device holder containing undergarment introduced in FIG. 1, including a tampon (shown in phantom) inserted in a tampon receiving pocket provided on the undergarment.

A first exemplary embodiment of a sanitary absorbent device holder containing undergarment 100 is illustrated in FIGS. 1 and 2. The undergarment 100 includes an undergarment body 101 which may be any suitable size and material such as cotton, polyester or cotton/polyester blend, for example. The undergarment body 101 may be any style of undergarment including but not limited to briefs, boxer shorts, bikini or thong. The undergarment body 101 includes a front body (anterior) portion 102, a rear body (posterior) portion 103 and side body portions 104 which connect the front body portion 102 and the rear body portion 103 defining a waist opening 105, as illustrated in FIG. 2. The front body portion 102 has an exterior surface 102a and an interior surface 102b as further illustrated in FIG. 2. The rear body portion 103 has an exterior surface 103a and an interior surface 103b. An elastic waistband 106 is preferably provided, circumscribing the waist opening 105.

A crotch portion 107 may connect the front body portion 102 and the rear body portion 103. Leg openings 108 are be defined by the front body portion 102, the rear body portion 103, the side body portions 104, and the crotch portion 107. An elastic leg band 109 is preferably provided, circumscribing each leg opening 108.

A pocket cover panel 114 is provided on the undergarment body 101. In some embodiments, the pocket cover panel 114 may be provided on the front body portion 102 of the undergarment body 101. In the embodiment illustrated in FIGS. 1 and 2, the pocket cover panel 114 is provided on the exterior surface 102a of the front body portion 102; however, in other embodiments the pocket cover panel 114 may be provided on the interior surface 102b of the front body portion 102 or in any other suitable location on the undergarment body 101. The pocket cover panel 114 may be attached to the undergarment body 101 by cover panel stitching 115 or other suitable attachment technique. Although the illustrated exemplary embodiment shows a free formed pocket cover panel 114, it is recognized the pocket cover panel 114 can be shaped to conform to seams of the undergarment body 101. As illustrated in FIG. 2, the pocket cover panel 114 has a cover panel interior 116. A cover panel interior surface 114a of the pocket cover panel 114 faces the cover panel interior 116.

A generally elongated tampon pocket 118 (shown in phantom in FIG. 1) is provided on the cover panel interior surface 114a of the pocket cover panel 114, or alternatively, on the exterior surface 102a of the front body portion 102 in the cover panel interior 116 of the pocket cover panel 114. The tampon pocket 118 may be attached to the pocket cover panel 114 by pocket stitching 119 or other suitable attachment technique. As illustrated in FIG. 1, in some embodiments a longitudinal axis of the tampon pocket 118 may be oriented in generally perpendicular relationship with respect to a longitudinal axis of the undergarment body 101. The tampon pocket 118 is sized to contain at least one tampon 120 (shown in phantom in FIG. 2).

In typical use, the sanitary absorbent device holder containing undergarment 100 is donned by a female wearer (not illustrated) and worn beneath the outer clothing (not illustrated) of the wearer. At least one tampon 120 (FIG. 2) is inserted in the tampon pocket 118 in the cover panel interior 116 of the pocket cover panel 114. When use of the tampon 120 is necessary, the wearer of the undergarment can easily remove the carried tampon 120 from the tampon pocket 118. It will be appreciated by those skilled in the art that the tampon 120 is discreetly and securely concealed in the tampon pocket 118 as the wearer wears the undergarment 100.

Figure 3:
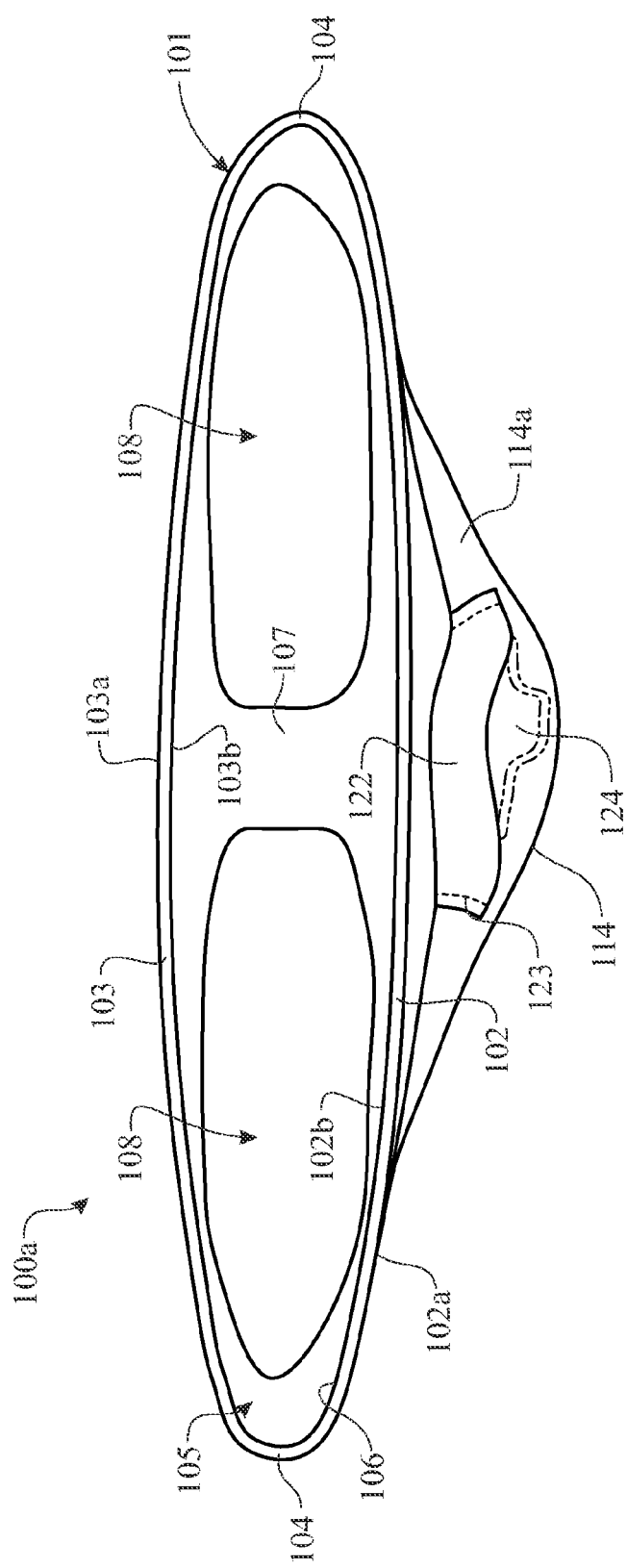
FIG. 3 presents a top perspective view of another exemplary embodiment of the undergarment with sanitary absorbent device holder, including a sanitary napkin (shown in phantom) inserted in a sanitary napkin pocket provided on the undergarment.

Another exemplary embodiment of a sanitary absorbent device holder containing undergarment 100a is illustrated in FIG. 3. The sanitary absorbent device holder containing undergarment 100a includes a sanitary napkin pocket 122, which is attached to the cover panel interior surface 114a of the cover panel 114 by any reasonable attachment interface, including pocket stitching 123, and the like. The sanitary napkin pocket 122 may have a generally elongated configuration and may be oriented in generally perpendicular relationship with respect to the longitudinal axis of the undergarment body 101 or plane defined by the waist opening 105. Accordingly, the sanitary napkin pocket 122 is sized to receive and conceal a sanitary napkin 124. When use of the tampon 120 is necessary, the wearer of the undergarment 100a can easily remove the carried sanitary napkin 124 from the sanitary napkin pocket 122.

Figure 4:
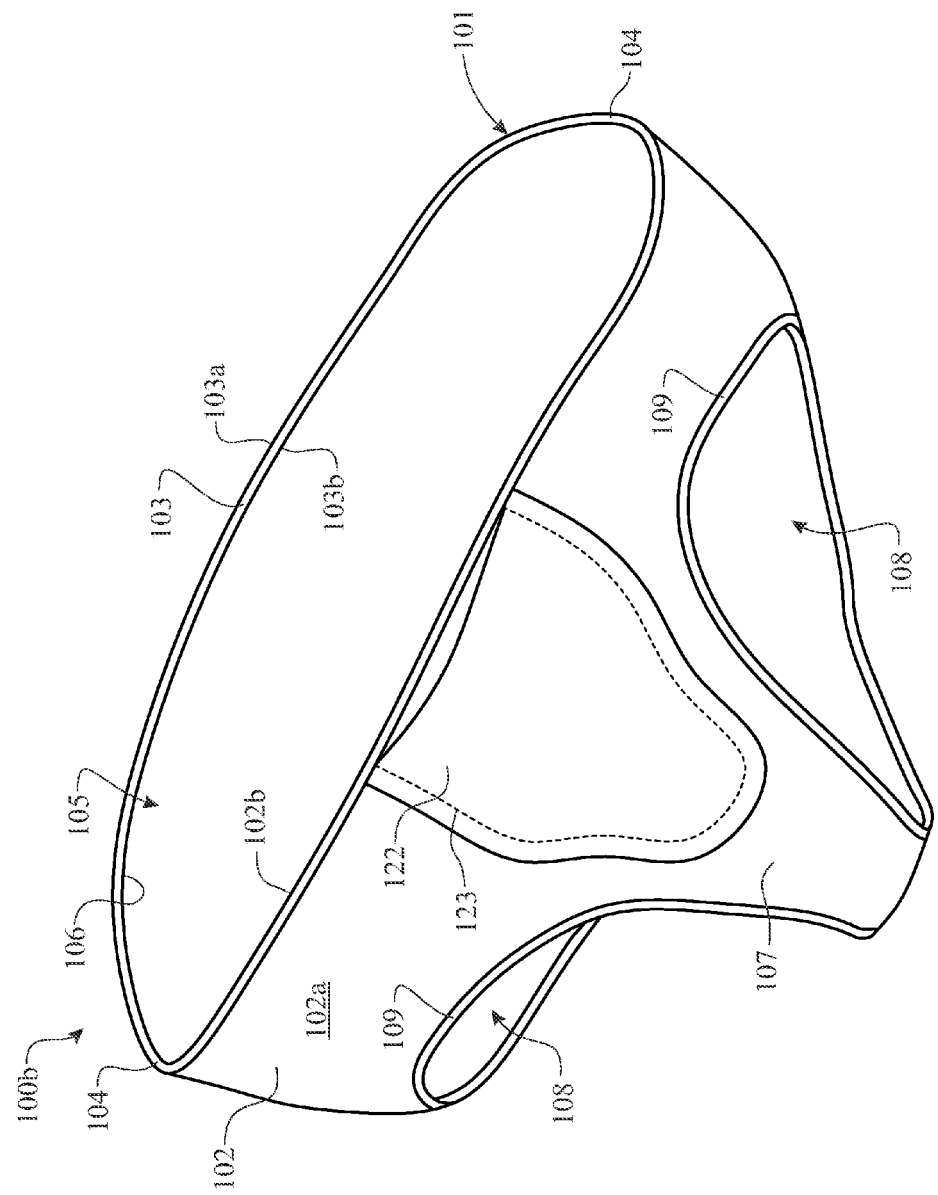
FIG. 4 presents a front perspective view of another exemplary embodiment of the undergarment with sanitary absorbent device holder, including a sanitary napkin pocket provided on an exterior surface of the undergarment.
Figure 5:
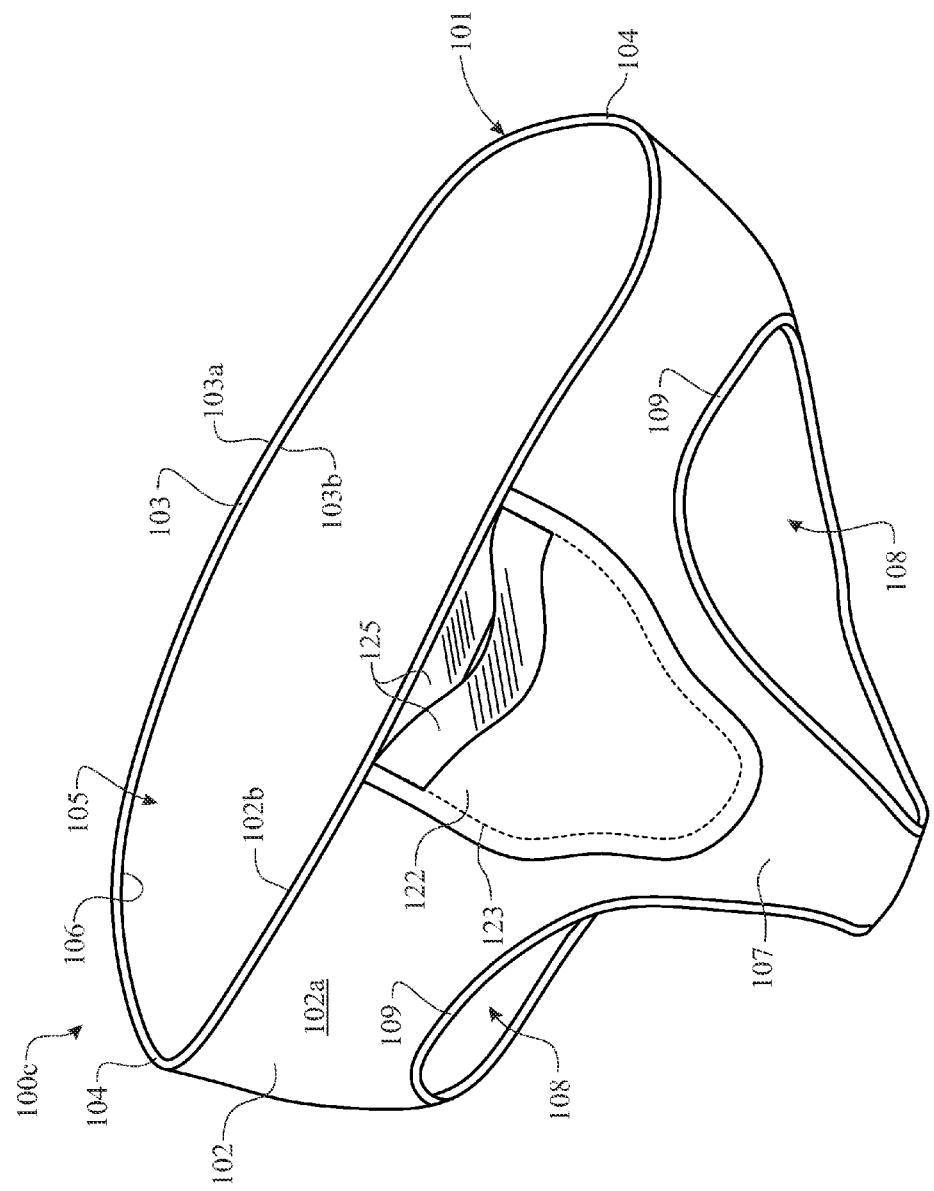
FIG. 5 presents a front perspective view of the exemplary embodiment of the sanitary absorbent device holder containing undergarment introduced in FIG. 4, the holder further comprising a closure strip.
Figure 6:
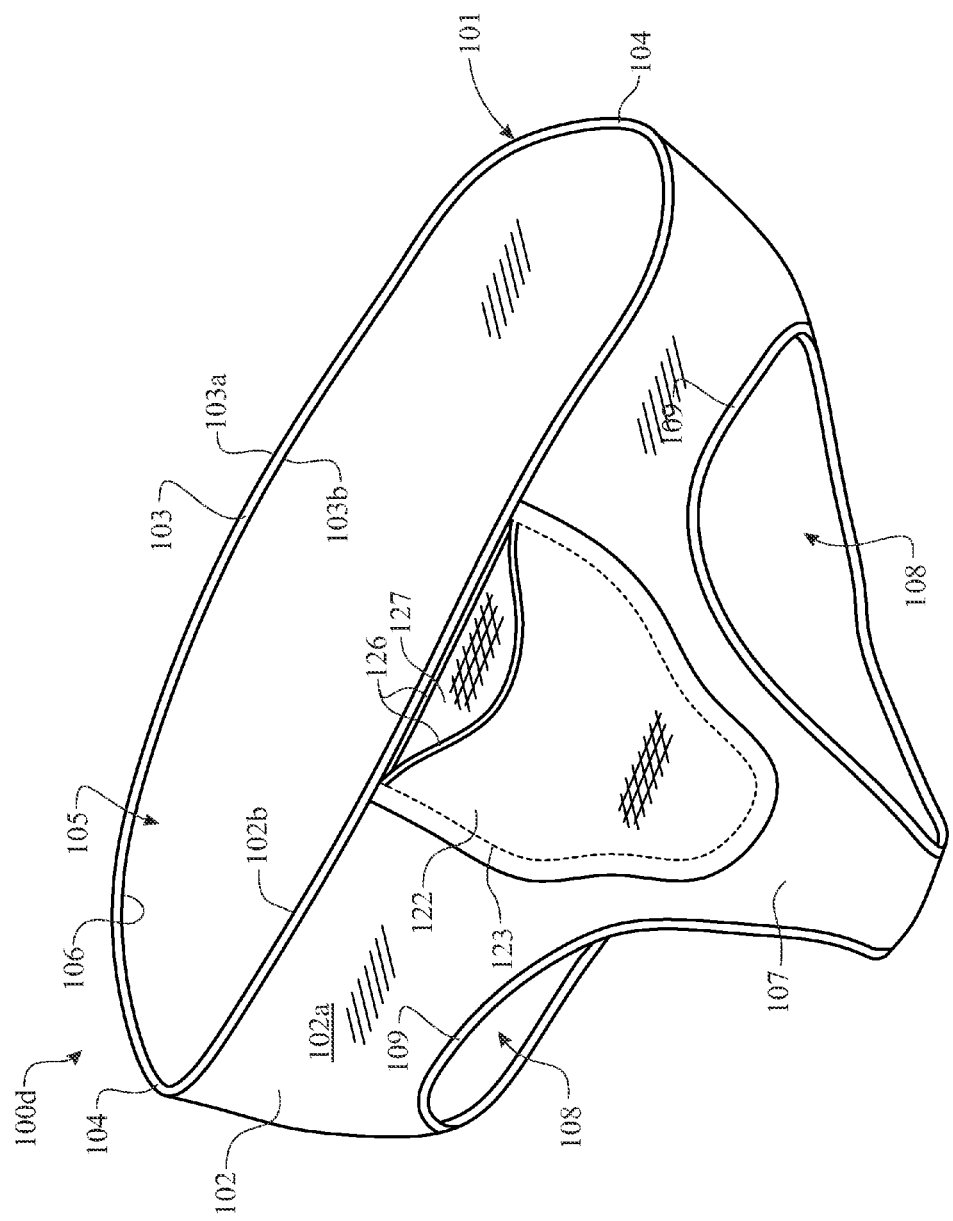
FIG. 6 presents a front perspective view of the exemplary embodiment of the sanitary absorbent device holder containing undergarment introduced in FIG. 4, the holder further comprising an alternative, interlocking closure strip.

Another exemplary embodiment of a sanitary absorbent device holder containing undergarment 100b is illustrated in FIGS. 4 through 6. The sanitary absorbent device holder containing undergarment 100b is a modified version of the sanitary absorbent device holder containing undergarment 100a. The sanitary absorbent device holder containing undergarment 100b excludes the pocket cover panel 114 (FIG. 3) and attaches the sanitary napkin pocket 122 directly to the exterior surface 102a of the front body portion 102 as illustrated. It is understood that the sanitary napkin pocket 122 can alternatively be attached at any other suitable location on the undergarment body 101.

Another exemplary embodiment of a sanitary absorbent device holder containing undergarment 100c is illustrated in FIG. 5. The sanitary absorbent device holder containing undergarment 100c is an enhanced version of the sanitary absorbent device holder containing undergarment 100b. The sanitary absorbent device holder containing undergarment 100c further comprises a closure interface 125 between the sanitary napkin pocket 122 and the undergarment body 101, respectively, to secure the sanitary napkin pocket 122 in a closed configuration. The closure interface 125 may be complementary dense hook and loop tape fastener sections, a zipper, snap(s), button(s), a frog-style enclosure (lace with a knot or button), or the like. It is also understood that the Another exemplary embodiment of a sanitary absorbent device holder containing undergarment 100d is illustrated in FIG. 6. The sanitary absorbent device holder containing undergarment 100d includes a pair of complementary interlocking closure strips 126 is provided on the sanitary napkin pocket 122 and the undergarment body 101, respectively, to seal the sanitary napkin 124 (FIG. 3) within the sanitary napkin pocket 122. A waterproof pocket liner 127 may line the interior surfaces of the sanitary napkin pocket 122, thus providing a moisture resistant or waterproof storage of the tampon 120 (FIG. 2) and/or the sanitary napkin 124 (FIG. 3).

Figure 7:
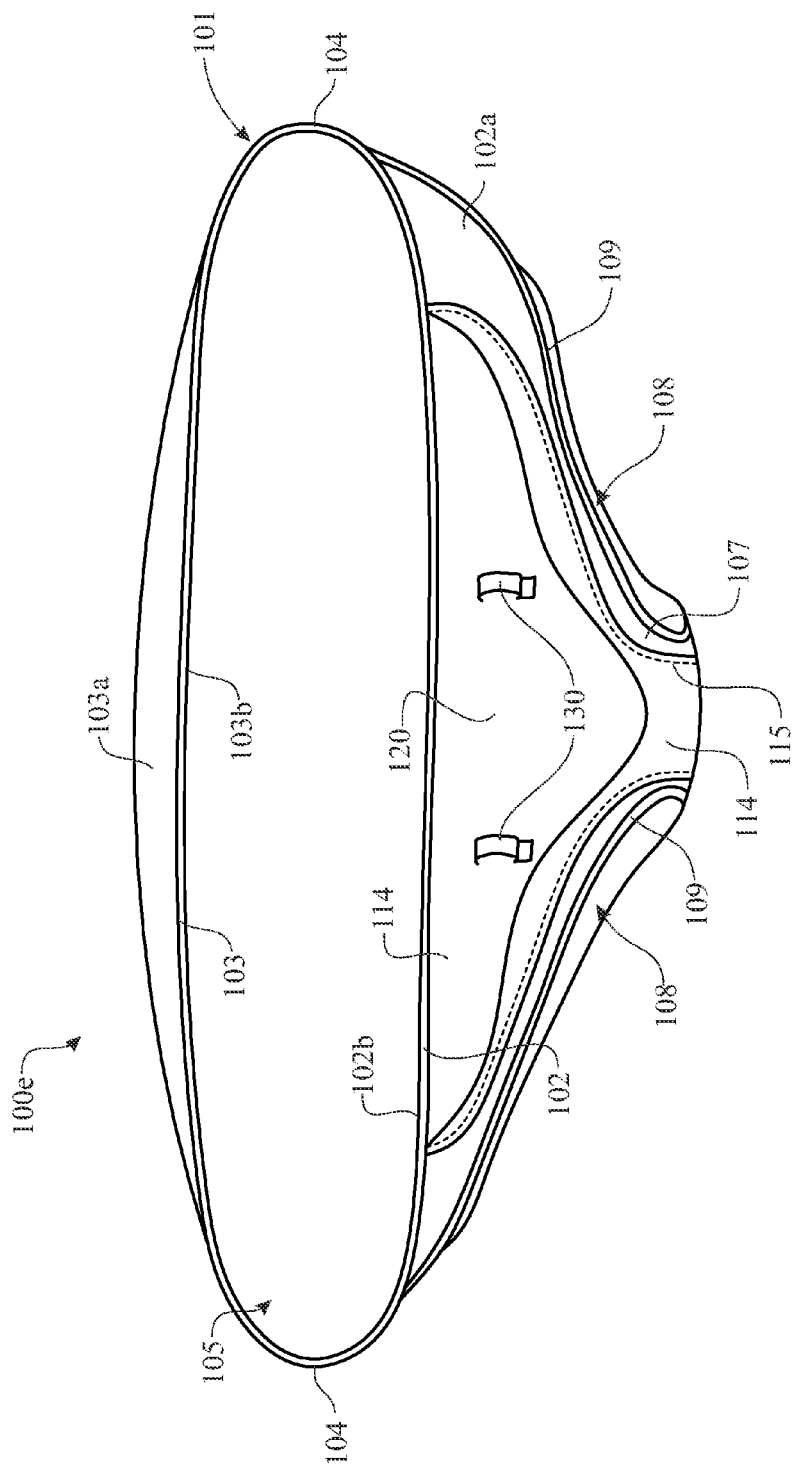
FIG. 7 presents a top perspective view of another exemplary embodiment of a sanitary absorbent device holder containing undergarment with, utilizing a pair of spaced-apart elastic bands provided on the undergarment and adapted to hold a tampon (shown in phantom)

Another exemplary embodiment of a sanitary absorbent device holder containing undergarment 100e is illustrated in FIG. 7. The sanitary absorbent device holder containing undergarment 100e includes a pair of spaced-apart elastic bands 130 is provided on the exterior surface 102a of the front body portion 102. It is understood that the spaced-apart elastic bands 130 can be attached at any other suitable location on the undergarment body 101, including along the sides or rear of the undergarment body 101, top or middle of the undergarment body 101, and the like. The elastic bands 130 may be attached to the front body portion 102 using stitching or any other suitable attachment technique known by those skilled in the art. A tampon 120 (shown in phantom) can be removably inserted into loops formed by the elastic bands 130. In some embodiments, a pocket cover panel 114 may be attached to the undergarment body 101 to cover and conceal the elastic bands 130 and the tampon 120. The spaced-apart elastic bands 130 can be oriented such to optimize the configuration. An example would be orienting the bands 130 such to contain the tampon 120 vertically when provided on a side portion of the undergarment body 101. It can also be placed vertically or horizontally on a rear portion of the undergarment body 101. Those skilled in the art can appreciate that the spaced-apart elastic bands 130 can be replaced by a frog style closure, ribbon, lacing, and the like to attach or secure the tampon 120 anywhere within the undergarment.

Another exemplary embodiment of a sanitary absorbent device holder containing undergarment 100f is illustrated in FIGS. 8 and 9. The sanitary absorbent device holder containing undergarment 100f includes a generally elongated, flexible scroll pocket 132 attached to the exterior surface 102a of the front body portion 102. It is understood that the generally elongated, flexible scroll pocket 132 can be attached at any other suitable location on the undergarment body 101, including along the sides or rear of the undergarment body 101, top or middle of the undergarment body 101, and the like. The scroll pocket 132 may include, for example, an attachment edge 133, which is attached to the undergarment body 101 by stitching or any other suitable attachment interface and a free edge 134, which is located opposite of the attachment edge 133. The scroll pocket 132 can be selectively deployed in a rolled configuration as illustrated in FIG. 8, in which the tampon 120 can be secured and concealed within the rolled scroll pocket 132, and an extended or unrolled configuration illustrated in FIG. 9, in which the tampon 120 can be removed from the scroll pocket 132 for use.

Figure 10:
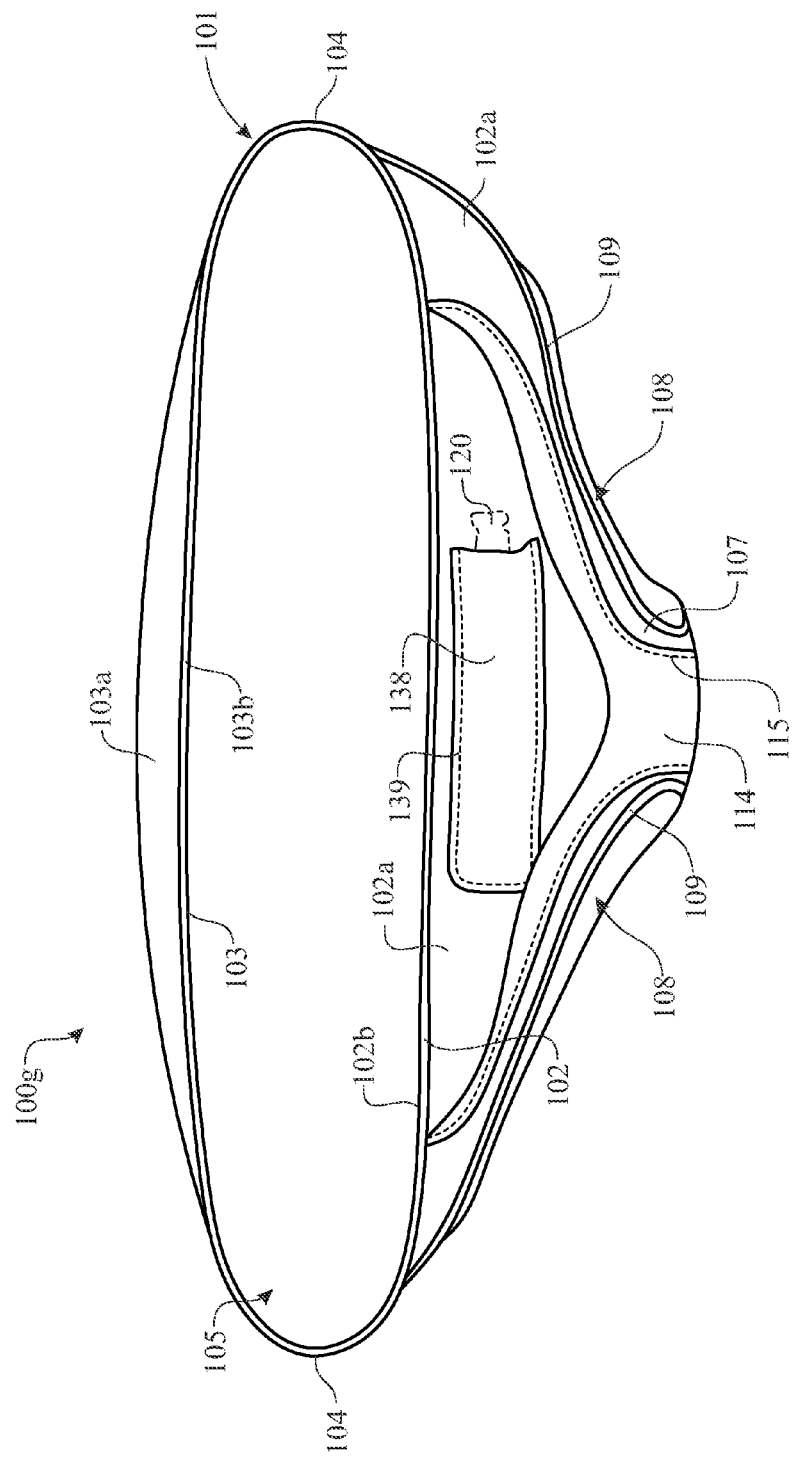
FIG. 10 presents a top perspective view of another exemplary embodiment of a sanitary absorbent device holder containing undergarment, incorporating a laterally-oriented tampon pocket attached to an exterior surface of the undergarment body and covered by a pocket cover panel.

Another exemplary embodiment of a sanitary absorbent device holder containing undergarment 100g is illustrated in FIG. 10. The sanitary absorbent device holder containing undergarment 100g includes a generally elongated tampon pocket 138 attached to the exterior surface 102a of the front body portion 102 of the undergarment body 101 using stitching or any other suitable attachment interface. It is understood that the generally elongated, flexible scroll pocket 132 can be attached at any other suitable location on the undergarment body 101, including along the sides or rear of the undergarment body 101, top or middle of the undergarment body 101, and the like. The longitudinal axis of the tampon pocket 138 may be oriented in generally parallel relationship with respect to the longitudinal axis of the undergarment body 101. A pocket cover panel 114 may be provided on the undergarment body 101 to conceal the tampon pocket 138.

Figure 11:
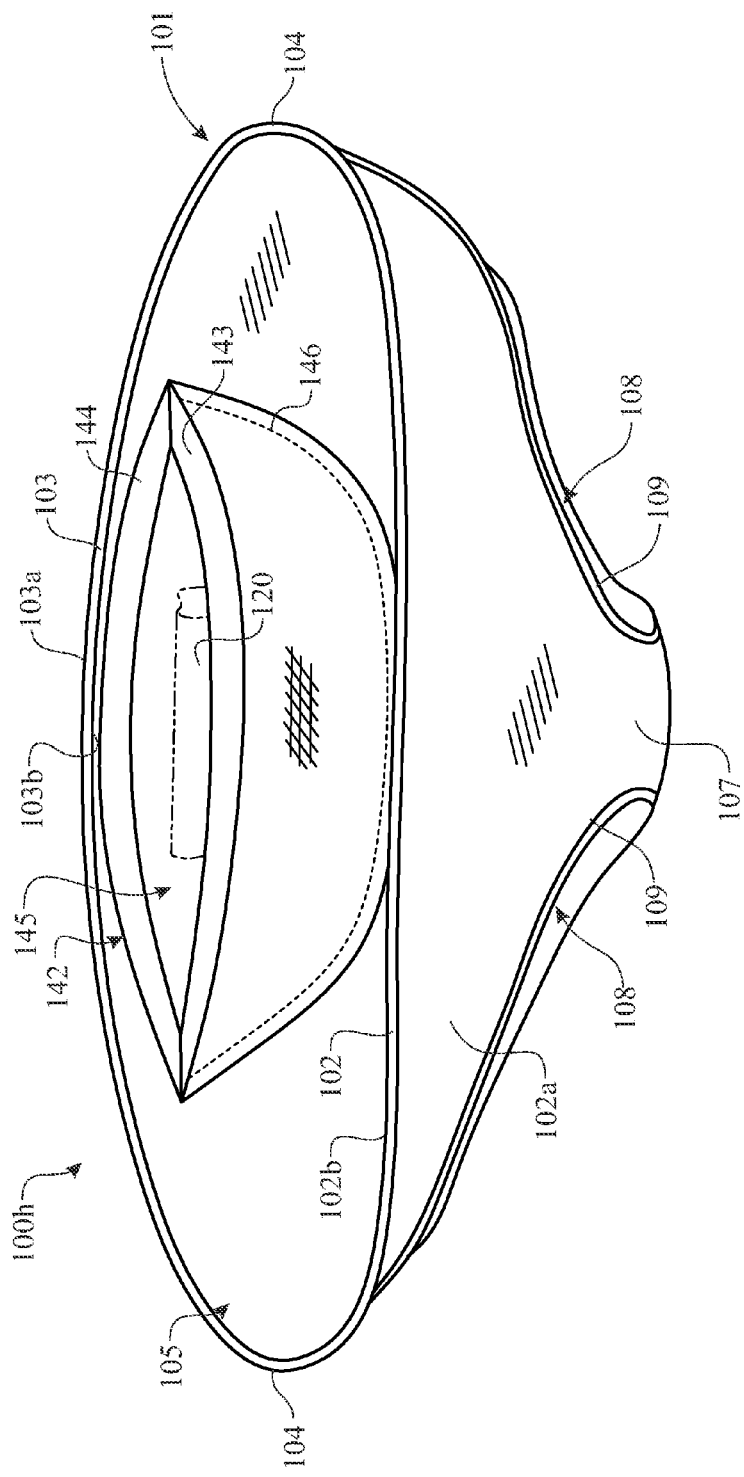
FIG. 11 presents a top perspective view of another exemplary embodiment of a sanitary absorbent device holder containing undergarment, with a tampon pocket provided on an interior portion of the undergarment.
Figure 12:
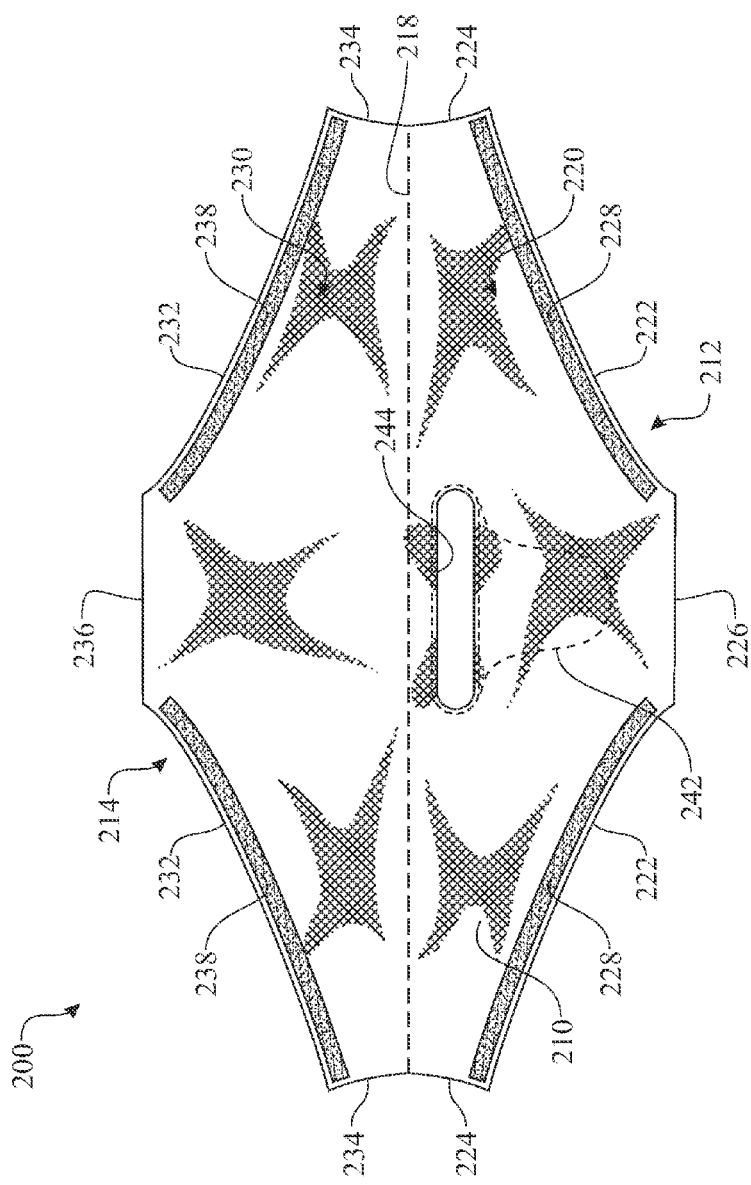
FIG. 12 presents a planar pocket concealing surface view of an exemplary independent attachment embodiment of an sanitary absorbent device holder undergarment accessory for attachment to a woman's underwear.
Figure 13:
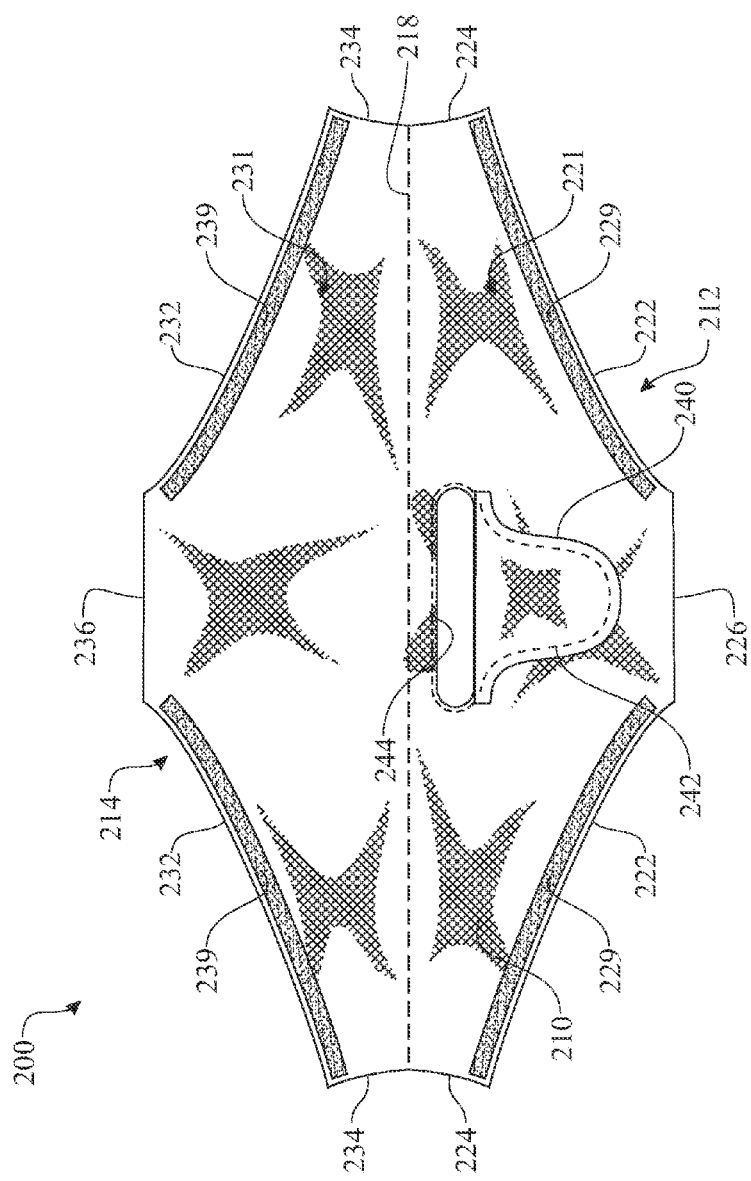
FIG. 13 presents a planar pocket exposing surface view of the exemplary sanitary absorbent device holder undergarment accessory introduced in FIG. 12.
Figure 14:
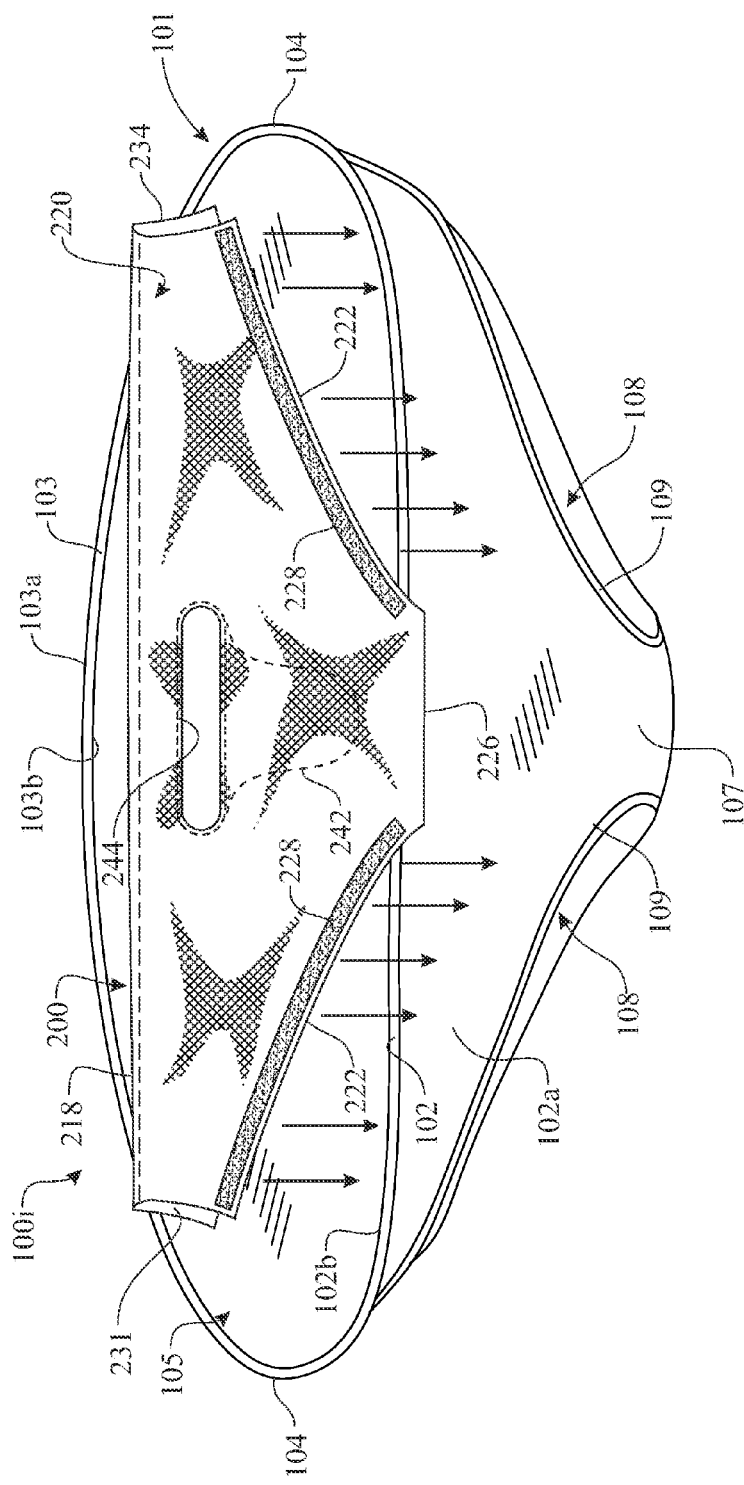
FIG. 14 presents a perspective view of the sanitary absorbent device holder undergarment accessory introduced in FIG. 12 being attached to the woman's underwear.
Figure 15:
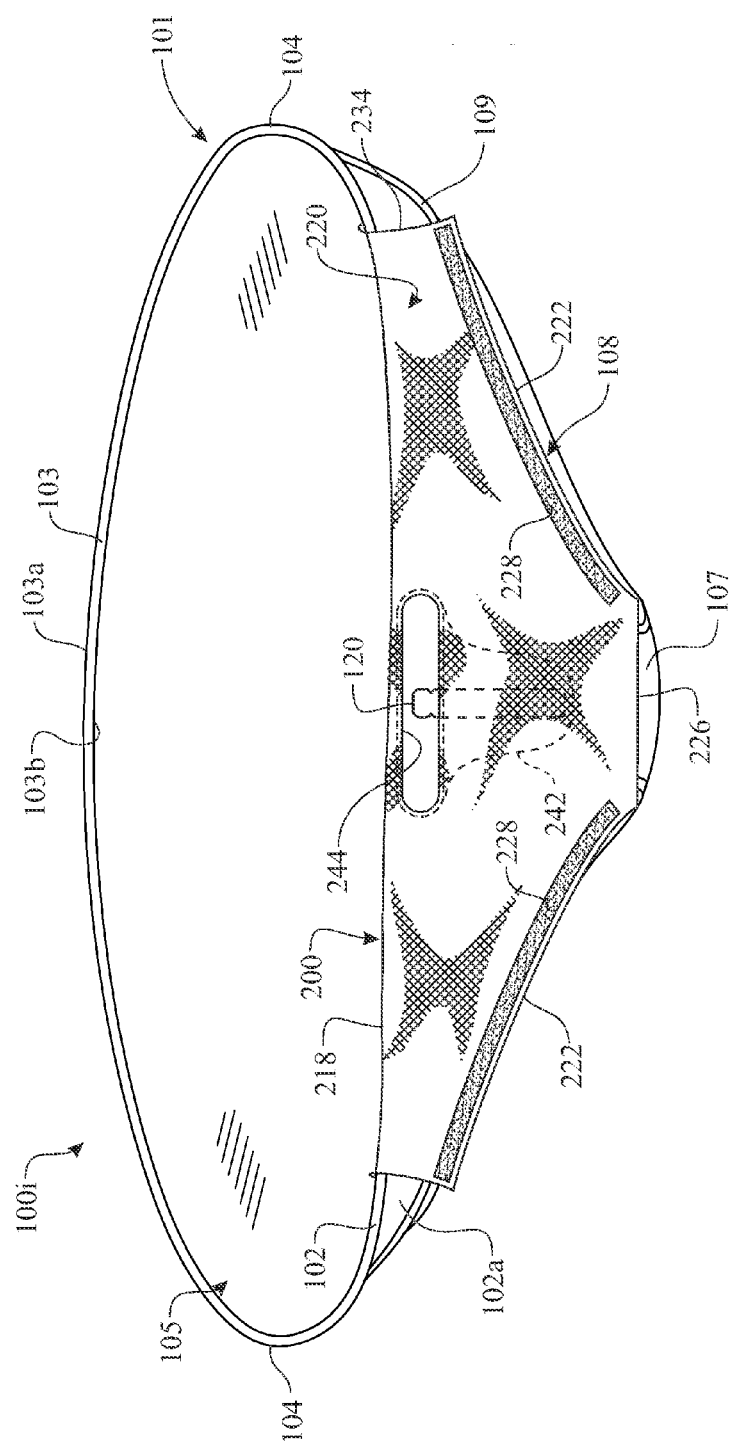
FIG. 15 presents a perspective view of the sanitary absorbent device holder undergarment accessory introduced in FIG. 12 attached to the woman's underwear and ready for use.

Another exemplary embodiment of a sanitary absorbent device holder containing undergarment 100h is illustrated in FIG. 11. The sanitary absorbent device holder containing undergarment 100h includes a sanitary absorbent device compartment 142 attached to the undergarment body 101. The sanitary absorbent device compartment 142 may include a rear compartment panel 144, which is attached to the interior surface 103b of the rear body portion 103 by stitching or any other reasonable attachment interface. A front compartment panel 143 may be sewn to the rear compartment panel 144 by compartment stitching 146 or any other reasonable attachment interface. The front compartment panel 143 and the rear compartment panel 144 define a compartment interior 145. Accordingly, one or multiple sanitary absorbent devices such as a tampon 120 (shown in phantom) and/or sanitary napkins 124 (FIG. 3) may be placed and concealed within the compartment interior 145 of the sanitary absorbent device compartment 142 until the wearer needs to use the sanitary absorbent device 120, 124. In alternative embodiments, the sanitary absorbent device compartment 142 may be attached to the exterior surface 103a of the rear body portion 103; to the exterior surface 102a or the interior surface 102b of the front body portion 102; or to any suitable alternative location on the undergarment body 101.

The present invention includes alternative embodiments, enabling a wearer to temporarily attach a sanitary absorbent device holder undergarment accessory 200 to the generic woman's underwear 100i as illustrated in FIGS. 12 through 15. The sanitary absorbent device holder undergarment accessory 200 is fabricated of a sanitary absorbent device holder carrier 210. The sanitary absorbent device holder carrier 210 is shaped to removably attach to the generic woman's underwear 100i. The sanitary absorbent device holder carrier 210 is segmented into a holder panel section 212 and a rear panel section 214 by a holder body waistband fold 218. The holder panel section 212 is fabricated of a flexible material having two sides, a first side is defined as a holder panel portion concealing surface 220 and a second side is defined as a rear panel portion concealing surface 230. The holder panel section 212 is bound by the holder body waistband fold 218; a centrally located holder panel crotch edge 226; a pair of holder panel leg band edges 222, each holder panel leg band edge 222 having a central end extending from a respective end of the holder panel crotch edge 226; and a holder panel side edge 224 extending between a distal end of the holder panel leg band edge 222 and a respective end of the holder body waistband fold 218. The holder panel section 212 is sized and shaped to contour to front body portion 102 or a rear body portion 103 of a pair of women's underwear. The sanitary absorbent device holder undergarment accessory 200 can include one or both of a holder panel concealing side attachment interface 228 and a holder panel exposing side attachment interface 229. Each holder panel concealing side attachment interface 228 would be attached to the holder panel portion concealing surface 220 proximate and preferably parallel to each respective holder panel leg band edge 222. Each holder panel exposing side attachment interface 229 would be attached to the holder panel portion exposing surface 221 proximate and preferably parallel to each respective holder panel leg band edge 222. The rear panel section 214 is bound by the holder body waistband fold 218; a centrally located rear panel crotch edge 236; a pair of rear panel leg band portions 232, each rear panel leg band portion 232 having a central end extending from a respective end of the rear panel crotch edge 236; and a rear panel side edge 234 extending between a distal end of the rear panel leg band portion 232 and a respective end of the holder body waistband fold 218. The rear panel section 214 is sized and shaped to contour to front body portion 102 or a rear body portion 103 of a pair of women's underwear. It is preferred that the holder panel section 212 and rear panel section 214 are of a similar shape and size. The sanitary absorbent device holder undergarment accessory 200 can include one or both of a rear panel concealing side attachment interface 238 and a rear panel exposing side attachment interface 239. Each rear panel concealing side attachment interface 238 would be attached to the rear panel portion concealing surface 230 proximate and preferably parallel to each respective rear panel leg band portion 232. Each rear panel exposing side attachment interface 239 would be attached to the rear panel portion exposing surface 231 proximate and preferably parallel to each respective rear panel leg band portion 232.

The holder panel attachment interfaces 228, 229 and the rear panel attachment interfaces 238, 239 are preferably fabricated of mating sections of dense hook and loop tape. Although the dense hook and loop tape is optimal, it is understood that other attachment interfaces can be employed by the designer, including ribbon, individual hook and loops, buttons, and the like.

A sanitary device holder 240 is provided for retaining the sanitary device 120, 124 until needed by the wearer. The sanitary device holder 240 can be provided in any of the previously disclosed form factors, including a pocket sized and configured to receive and retain the sanitary device 120, 124, one or more loops configured to receive and retain the sanitary device 120, 124, a scrolling styled receptacle configured to receive and retain the sanitary device 120, 124 and the like. The sanitary device holder 240 is preferably located at a central position of the holder panel section 212 and attached to the holder panel portion exposing surface 221 using sanitary device holder attachment stitching 242. The sanitary device holder attachment stitching 242 defines an opening for insertion of the sanitary device 120, 124. A holder access port 244 is provided through the sanitary absorbent device holder carrier 210 at a location to provide the user with access to the opening of the sanitary device holder 240 from the holder panel portion concealing surface 220. The holder access port 244 can be reinforced by stitching or any other known garment reinforcement technology. Although the illustrated embodiment presents the sanitary device holder 240 at a central location, it is understood that the sanitary device holder 240 can be located at any reasonable position upon the holder panel section 212.

The user can elect to place the sanitary absorbent device holder undergarment accessory 200 onto the sanitary absorbent device holder containing undergarment 100i in either an exposed (not shown) or a concealed (shown in FIG. 14) orientation. The sanitary absorbent device holder undergarment accessory 200 is folded into an inverted "U" shape along the holder body waistband fold 218 and positioned straddling either a front portion or a rear portion of the front body portion 102. The holder panel portion concealing surface 220 is positioned outside of the generic woman's underwear 100i and the rear panel portion concealing surface 230 is positioned within the interior portion defined by the waist opening 105. The sanitary absorbent device holder undergarment accessory 200 is lowered resting the holder body waistband fold 218 upon the front body portion 102. The holder panel attachment interface 228, 229 and the respective rear panel attachment interface 238, 239 are positioned proximate the elastic leg band 109 and subsequently engaged to retain the sanitary absorbent device holder undergarment accessory 200 in position on the generic woman's underwear 100i. Providing the holder panel attachment interfaces 228, 229 and the respective rear panel attachment interfaces 238, 239 on both the concealed surfaces 220, 230 and the exposing surface 221, 231 enables the wearer to vary the attachment interface configuration to optimize comfort. For example, the holder panel concealing side attachment interface 228 and the rear panel concealing side attachment interface 238 can be engaged together, the holder panel concealing side attachment interface 228 and the rear panel exposing side attachment interface 239 can be engaged together, or the holder panel exposing side attachment interface 229 and the rear panel exposing side attachment interface 239 can be engaged together. The exemplary illustration engages the holder panel exposing side attachment interface 229 and rear panel exposing side attachment interface 239 together. The crotch portion 107 remains sandwiched between the holder panel crotch edge 226 and the rear panel crotch edge 236.

Access to the sanitary device holder 240 is provided through the holder access port 244. The user would draw a lower portion of the holder access port 244 forward, spread an upper edge of the sanitary device holder 240 from the holder panel portion exposing surface 221, and insert the sanitary device 120, 124 therein. When the wearer needs to acquire and use the sanitary device 120, 124, the wearer would remove the sanitary device 120, 124 from the sanitary device holder 240.

Figure 16:
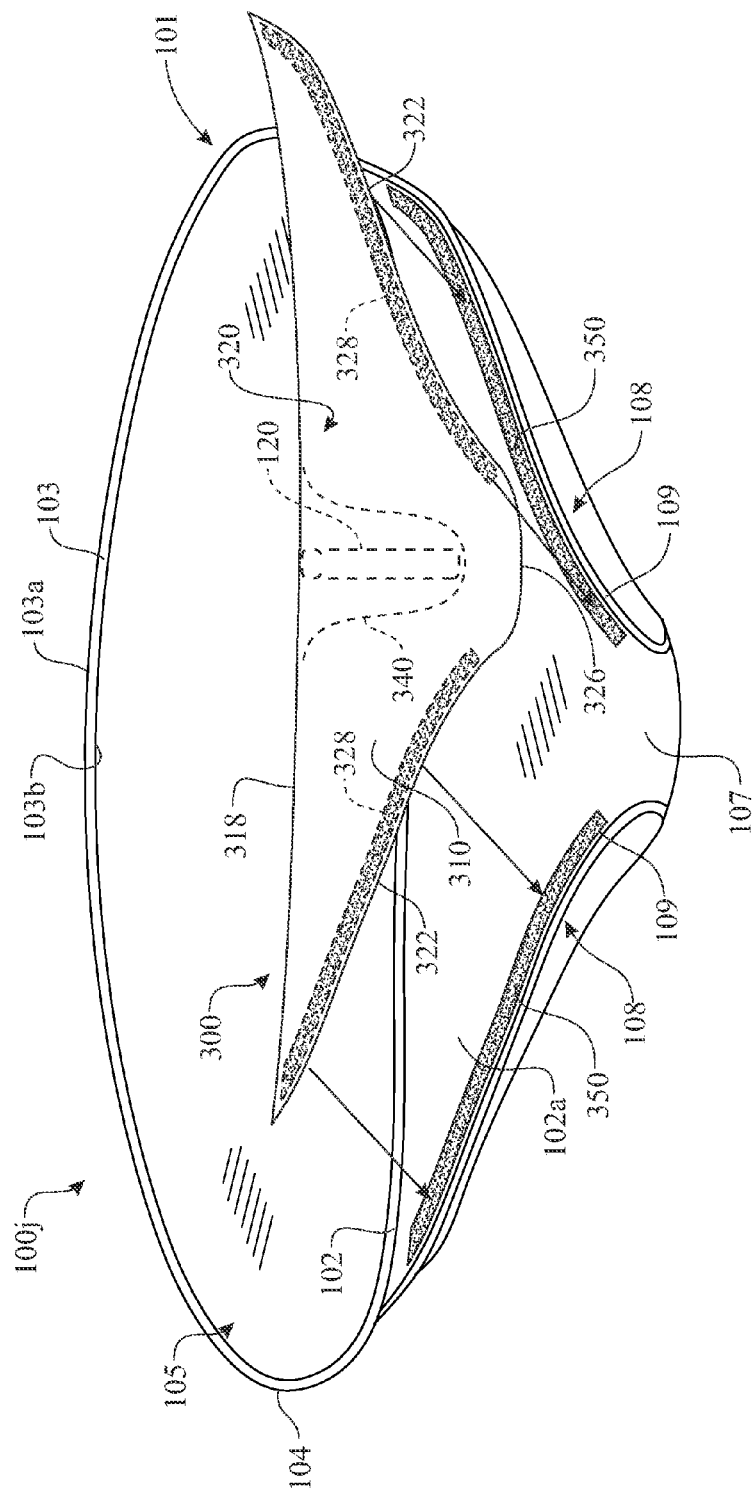
FIG. 16 presents a perspective view of an exemplary direct attachment embodiment of a sanitary absorbent device holder undergarment accessory.

The sanitary absorbent device holder undergarment accessory 200 is configured for attachment to any respectfully dimensioned generic woman's underwear 100*i*. An alternative to the sanitary absorbent device holder undergarment accessory 200 is a sanitary absorbent device holder undergarment accessory 300, wherein the sanitary absorbent device holder undergarment accessory 300 is directly attached to a pocket panel receiving underwear 100*j*, as illustrated in FIG. 16. The pocket panel receiving underwear 100*j* includes a mating attachment interface 350 attached to the front body portion 102 and/or rear body portion 103 of the undergarment body 101 at a location adjacent to each elastic leg band 109. The sanitary absorbent device holder undergarment accessory 300 includes a sanitary absorbent device holder carrier 310 dimensioned and shaped to mate with a front body portion 102 or a rear body portion 103 of the pocket panel receiving underwear 100*j*. The sanitary absorbent device holder carrier 310 can be referenced having a holder panel exposed surface 320 and a concealed surface (opposite of the holder panel exposed surface 320). The sanitary absorbent device holder carrier 310 is bound by a sanitary absorbent device holder carrier waistband edge 318; a centrally located holder panel crotch edge 326; a pair of holder panel leg band edges 322, each holder panel leg band edge 322 extending between a respective end of the holder panel crotch edge 326 and a respective end of the sanitary absorbent device holder carrier waistband edge 318. The sanitary absorbent device holder undergarment accessory 300 includes a pair of holder panel concealing side attachment interfaces 328, each holder panel concealing side attachment interface 328 is attached to an interior surface of the sanitary absorbent device holder carrier 310 at a location adjacent to each holder panel leg band edge 322. A sanitary device holder 340 is attached to the interior surface of the sanitary absorbent device holder carrier 310, preferably at a central location of the sanitary absorbent device holder carrier 310. Although the illustrated embodiment presents the sanitary device holder 340 at a central location, it is understood that the sanitary device holder 340 can be located at any reasonable position upon the sanitary absorbent device holder carrier 310. It is understood that the sanitary device holder 340 can be assembled to either side of the sanitary absorbent device holder carrier 310. It is understood that the holder panel concealing side attachment interface 328 can be provided on either or both sides of the sanitary absorbent device holder carrier 310. An embodiment providing the holder panel concealing side attachment interface 328 on both sides of the sanitary absorbent device holder carrier 310 enables flexibility to the end user on how they want to configure the location of the sanitary device holder 340. This embodiment enables the end user the ability to attach the sanitary absorbent device holder undergarment accessory 300 to the pocket panel receiving underwear 100*j* with the sanitary device holder 340 in an exposed orientation or a concealed orientation.

In use, the sanitary absorbent device holder undergarment accessory 300 is attached to the pocket panel receiving underwear 100*j* by engaging each holder panel concealing side attachment interface 328 on one side of the sanitary absorbent device holder carrier 310 with the respective mating attachment interface 350 on the pocket panel receiving underwear 100*j*. The user would insert a sanitary device 120, 124 into the sanitary device holder 340. Access to the sanitary device holder 340 is provided by a space created between the front body portion 102 and the sanitary absorbent device holder carrier waistband edge 318.

The illustrated embodiment includes a gap between the sanitary absorbent device holder carrier waistband edge 318 and the exterior surface 102*a*, providing access to the sanitary device holder 340. Those skilled in the art would understand that a resealable closure can be provided between the sanitary absorbent device holder carrier waistband edge 318 and the exterior surface 102*a* as desired.

Figure 17:
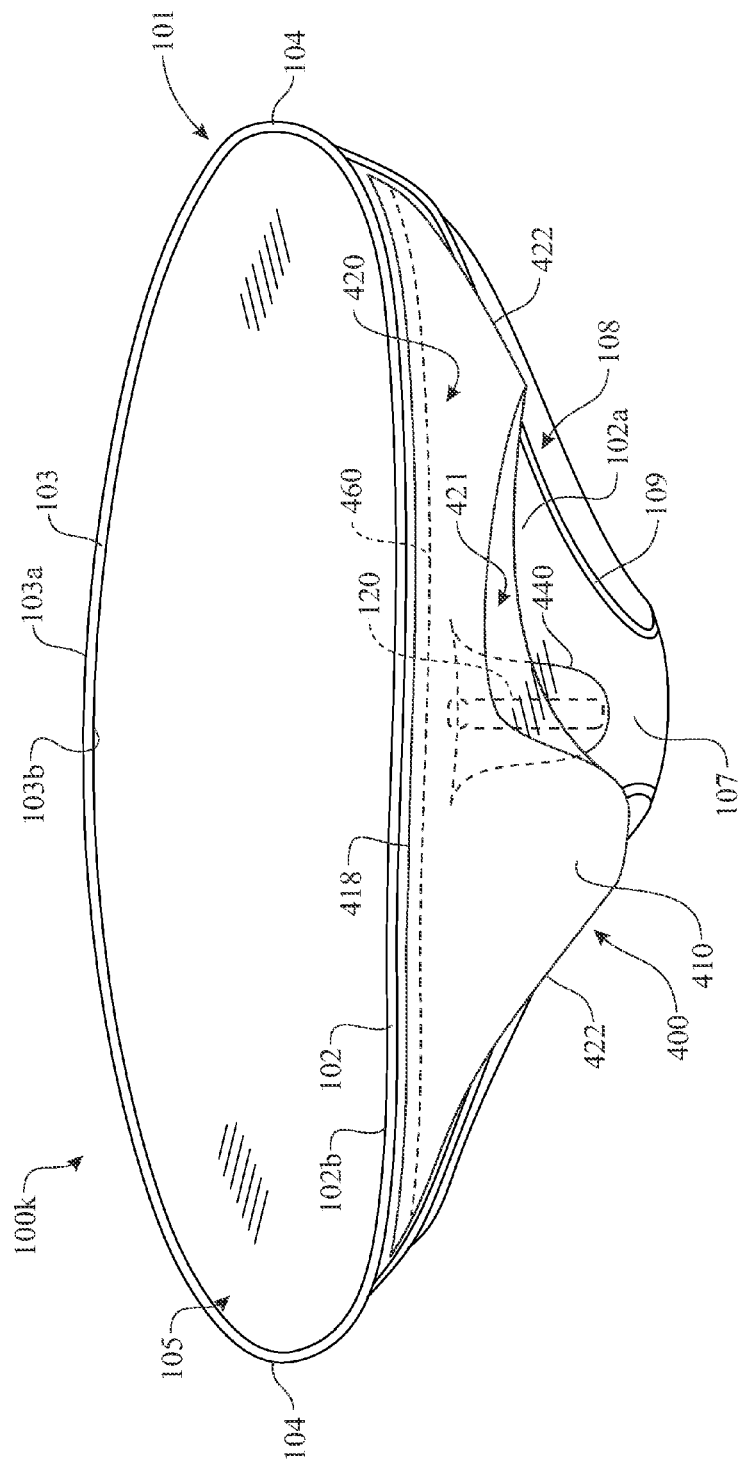
FIG. 17 presents a perspective view of an exemplary concealed embodiment of a sanitary absorbent device holder comprising undergarment.

A sanitary absorbent device holder containing undergarment 100*k* is representative of yet another exemplary embodiment, integrating a sanitary device holder 440 onto an outer surface of the undergarment body 101, as illustrated in FIG. 17. The sanitary device holder 440 is preferably attached to the front body portion 102 of the undergarment body 101. The sanitary absorbent device holder cover panel 400 includes a sanitary absorbent device holder cover body 410 dimensioned and shaped to mate with a front body portion 102 or a rear body portion 103 of the sanitary absorbent device holder containing undergarment 100*k*. The sanitary absorbent device holder cover body 410 can be referenced having a holder panel exposed surface 420 and a holder panel concealed surface 421 (opposite of the holder panel exposed surface 420). The sanitary absorbent device holder cover body 410 is bound by a sanitary absorbent device holder cover body waistband edge 418 and a holder panel leg band edge 322 collectively defining a peripheral edge thereof. The sanitary absorbent device holder cover body 410 is designed for attachment to the undergarment body 101 along the front body portion 102 via a mating attachment interface 460 and hangs downward covering the sanitary device holder 440. The mating attachment interface 460 is preferably stitching, but can be any attachment interface suitable for the application. The sanitary absorbent device holder cover body 410 is fabricated of a flexible material and finished to avoid fraying along the holder panel unsecured edge 422.

In use, the wearer would raise the sanitary absorbent device holder cover body 410 upwards, exposing the sanitary device holder 440. The sanitary device 120, 124 is then inserted and stored within the sanitary device holder 440. The sanitary absorbent device holder cover body 410 is released, allowing the sanitary absorbent device holder cover body 410 to fall covering and thus concealing the sanitary device holder 440. When the sanitary device 120, 124 is needed, the user raises the sanitary absorbent device holder cover body 410, exposing the sanitary device holder 440 and subsequently removes the sanitary device 120, 124 from the sanitary device holder 440. The sanitary absorbent device holder cover body 410 is again released, allowing the sanitary absorbent device holder cover body 410 to return to the naturally covering configuration.

The exemplary embodiment locates the sanitary device holder 440 upon the front body portion 102. It is understood that the sanitary device holder 440 can be attached to the undergarment body 101 along either side 104 or along the rear body portion 103, wherein the sanitary absorbent device holder cover body 410 would be assembled to the undergarment body 101 at a location providing the same concealing function as previously described.

Although the illustrated embodiments present a single sanitary device holder 118, 122, 130, 132, 138, 240, 340 centrally positioned, it is understood that the sanitary device holder 118, 122, 130, 132, 138, 240, 340 can be located at any reasonable location. Although the illustrated embodiments present a single sanitary device holder 118, 122, 130, 132, 138, 240, 340, it is understood that the embodiments may include multiple sanitary device holders 118, 122, 130, 132, 138, 240, 340. The disclosure presents a primary application for a sanitary device holder 118, 122, 130, 132, 138, 240, 340 for use in conjunction with a pair of woman's underwear. It is well understood that the same concept can be applied to and utilized in conjunction with boxers, briefs, unisex undergarments, and the like.

The various embodiments can include a closure at any reasonable location to secure either the carrier and undergarment together, the pocket, a cover over the pocket, the cover panel, and the like. The closure can be of any known closure style. The design can include features to ensure the sanitary device holder 118, 122, 130, 132, 138, 240, 340 retains the sanitary device 120, 124 remains in a moisture free environment.

Since many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalence.

I claim:

1. A sanitary absorbent device holder undergarment accessory, comprising:
    a sanitary absorbent device holder carrier having a first side and a second side;
    said sanitary absorbent device holder carrier segmented into a holder panel section and a rear panel section by a waistband fold, each panel section being bound by:
      said waistband fold,
      a pair of side edges, each side edge extending from a respective end of said waistband fold,
      a pair of leg band edges, each leg band edge extending from a distal end of each holder panel side edge, and
      a holder panel crotch edge extending between central ends of each of said leg band edges;
    an attachment interface provided between said holder panel section leg band edge and a mating rear panel section leg band edge; and
    a sanitary device holder attached to a first side of said holder panel section,
    wherein said sanitary absorbent device holder carrier is designed to be folded along said waistband fold, placed straddling said waistband fold over a waistband of a woman's underwear and secured in located by engaging said attachment interface between said holder panel section leg band edge and said mating rear panel section leg band edge at a position proximate a leg opening of said woman's underwear.

2. A sanitary absorbent device holder undergarment accessory as recited in claim 1 further comprising a holder access port located through said first side proximate said sanitary device holder, enabling insertion of a sanitary device into said sanitary device holder through said holder access port.

3. A sanitary absorbent device holder undergarment accessory as recited in claim 1, wherein said sanitary device holder is provided in a form of a pocket, wherein said pocket is sized and configured to receive at least one of a sanitary napkin and a tampon.

4. A sanitary absorbent device holder undergarment accessory as recited in claim 3, said pocket further comprises a closure mechanism.

5. A sanitary absorbent device holder undergarment accessory as recited in claim 4, said pocket and closure mechanism combined form a moisture barrier for contents stored within said pocket.

6. A sanitary absorbent device holder undergarment accessory as recited in claim 1, wherein said sanitary device holder comprises a pair of spaced-apart elastic bands sized and configured to receive a tampon.

7. A sanitary absorbent device holder undergarment accessory as recited in claim 1, wherein said sanitary device holder comprises a scrolling pocket style and configured to receive a tampon.

8. A sanitary absorbent device holder undergarment accessory as recited in claim 1, wherein said attachment interface is a dense hook and loop tape interface assembled to said sanitary absorbent device holder carrier at a location adjacent to each holder panel leg band edge.

9. A sanitary absorbent device holder undergarment accessory as recited in claim 1, wherein said attachment interface is a dense hook and loop tape interface assembled to said first side of said sanitary absorbent device holder carrier at a location adjacent to each holder panel leg band edge and to said second side of said sanitary absorbent device holder carrier at a location adjacent to each holder panel leg band edge.

* * * * *